(12) United States Patent
Weiner

(10) Patent No.: US 7,592,012 B2
(45) Date of Patent: Sep. 22, 2009

(54) CHIMERIC PROTEINS FOR CELL TARGETING AND APOPTOSIS INDUCTION AND METHODS OF USING THE SAME

(75) Inventor: David B. Weiner, Merion Station, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 732 days.

(21) Appl. No.: 10/478,741

(22) PCT Filed: May 28, 2002

(86) PCT No.: PCT/US02/16680

§ 371 (c)(1), (2), (4) Date: May 11, 2004

(87) PCT Pub. No.: WO02/097042

PCT Pub. Date: Dec. 5, 2002

(65) Prior Publication Data

US 2004/0181041 A1    Sep. 16, 2004

Related U.S. Application Data

(60) Provisional application No. 60/293,794, filed on May 25, 2001.

(51) Int. Cl.
*A61K 39/00* (2006.01)
*A61K 39/12* (2006.01)
*C12Q 1/70* (2006.01)

(52) U.S. Cl. ............. 424/192.1; 424/204.1; 424/218.1; 424/277.1; 435/5

(58) Field of Classification Search ....................... None
See application file for complete search history.

(56) References Cited

U.S. PATENT DOCUMENTS

| 5,910,486 | A | * | 6/1999 | Curiel et al. .................. 514/44 |
| 6,645,490 | B2 | * | 11/2003 | Yarkoni et al. ............ 424/134.1 |
| 7,125,957 | B1 | | 10/2006 | Aida et al. |
| 2002/0090374 | A1 | | 7/2002 | Yarkoni et al. |
| 2002/0164349 | A1 | | 11/2002 | Weiner et al. |
| 2004/0028651 | A1 | | 2/2004 | Muthumani et al. |

FOREIGN PATENT DOCUMENTS

| WO | WO 96/38571 | 12/1996 |
| WO | WO99/45128 | 9/1999 |
| WO | 0018426 | 4/2000 |
| WO | WO02/28165 | 4/2002 |

OTHER PUBLICATIONS

Aqeilan et al., "Interleukin 2-Bax: a novel prototype of human chimeric proteins for targeted therapy," *FEBS Letters* (1999) 457(2):271-276.

Azar et al., "GnRH-Bik/Bax/Bak chimeric proteins target and kill adenocarcinoma cells; the general use of pro-apoptotic proteins of the Bcl-2 family as novel killing components of targeting chimeric proteins," *Apoptosis* (2000) 5(6):531-542.

European Search Report Dated Dec. 3, 2004 for EP Application No. 02 74 1737.

Pletnev, et al., "West Nile virus/dengue type 4 virus chimeras that are reduced in neurovirulence and peripheral virulence without loss of Immunogenicity or protective efficacy," Proc. Natl. Acad. Sci. USA (2002) 99:3036-3041.

Pletnev, et al., "West Nile virus/dengue type 4 virus chimeras that are reduced in neurovirulence and peripheral virulence without loss of Immunogenicity or protective efficacy," Proc. Natl. Acad. Sci. (2002) 99:3036-3041.

Telford, et al., "The murine interleukin 1beta gene: structure and evolution," Nucleic Acids Res. (1986) 14:9955-9963.

Tanabe, et al., "Molecular cloning and structure of the interleukin-5 gene," J. Biol. Chem. (1987) 262:16580-16584.

Yokota, et al., "Isolation and characterization of lymphokine cDNA clones encoding mouse and human IgA-enchancing factor and eosinophil colony-stimulating factor activities: relationship to interleukin-5," Proc. Natl. Acad. Sci. USA (1987) 84:7388-7392.

Campbell, et al., "Molecular cloning, nucleotide sequence, and expression of the gene encoding human eosinophil differentiation factor (interleukin 5)," Proc. Natl. Acad. Sci. USA (1987) 84:6629-6633.

Yokota, et al., "Isolation and characterization of a human interleukin cDNA clone, homologous to mouse B-cell stimulatory factor 1, that expresses B-cell- and T-cell-stimulating factor," Proc. Natl. Acad. Sci. USA (1986) 83:5894-5898.

Otsuka, et al., "Structural analysis of the mouse chromosomal gene encoding interleukin 4 which expresses B cell, T cell and mast cell stimulating activities," Nucleic Acids Res. (1987) 15:333-344.

Devos, et al., "Molecular cloning of human interleukin 2 cDNA and its expression in *E. coli*," Nucleic Acids Res. (1983) 11:4307-4323.

Fuse, et al., "Organization and structure of the mouse interleukin-2 gene," Nucleic Acids Res. (1984) 12:9323-9331.

Fujita, et al., "Structure of the human interleukin gene," Proc. Natl. Acad. Sci. USA (1983) 80:7437-7441.

Holbrook, et al., "T-cell growth factor: complete nucleotide sequence and organization of the gene in normal and malignant cells," Proc. Natl. Acad. Sci. USA (1984) 81:1634-1638.

Furutani, et al., "Complete nucleotide sequence of the gene for human interleukin 1 alpha," Nucleic Acids Res. (1986) 14:3167-3179.

March, et al., "Cloning, sequence and expression of two distinct human intereukin-1 complementary DNAs," Nature (1985) 315:641-647.

Taniguchi, et al., "Structure and expression of a cloned cDNA for human interleukin-2," Nature (1983) 302:305-310.

(Continued)

Primary Examiner—Stacy B Chen
(74) Attorney, Agent, or Firm—Pepper Hamilton LLP

(57) ABSTRACT

Fusion proteins which comprise an apoptosis inducing protein portion and a cell targeting portion are disclosed. Fusion proteins which comprise a protease portion and a cell targeting portion are disclosed. Compositions for and methods of targeting and inducing the death of cells are disclosed.

20 Claims, No Drawings

OTHER PUBLICATIONS

Maeda, et al., "Cloning of intereukin-2 mRNAs from human tonsils," Biochem. Biophys. Res. Comm. (1983) 115:1040-1047.

Arai, et al., "Complete nucleotide sequence of the chromosomal gene for human IL-4 and its expression," J. Immunol. (1989) 142:274-282.

Noma, et al., "Cloning of cDNA encoding the murine lgG1 induction factor by a novel strategy using SP6 promoter," Nature (1984) 319:640-646.

Campbell, et al., "Isolation, structure and expression of c-DNA and genomic clones for murine eosinophil differentiation factor. Comparison with other eosinophilopoietic lymphokines and identity with interleukin-5," Eur. J. Biochem. (1988) 174:345-352.

Grabstein, et al., "Cloning of a t-cell growth factor that interacts with the beta chain of the interleukin-2 receptor," Science (1994) 264:965-968.

Ushio, et al., "Cloning of the cDNA for human IFN gamma-inducing factor expression in *Escherichia coli*, and studies of the biologic activities of the protein," J. Immunol. (1996) 156:4274-4279.

Pennica, "Human tumor necrosis factor: precursor structure, expression and homology to lymphotoxin," Nature (1984) 312:724-729.

Gray, "Cloning and expression of cDNA for human lymphotoxin, a lymphokine with tumor necrosis activity," Nature (1984) 312:721-724.

Utz and Anderson, "Life and death decisions: regulation of apoptosis by proteolysis of signaling molecules," Cell Death Differ. (2000) 7:589-602.

Sambrook, et al., Molecular Cloning: A Laboratory Manual ($2^{nd}$ Ed.), Cold Spring Harbor Laboratory Press, Clod Spring Harbor, NY, 1989.

Ausubel, et al., eds., Current Protocols in Molecular Biology, Wiley and Sons, NY, 2000.

Glover, ed., DNA Cloning: A Practical Approach, vols. 1 and II.

Colwick and Kaplan, eds., Methods in Enzymology, Academic Press.

Weir and Blackwell, eds., Handbook of Experimental Immunology, vols. I-IV, Blackwell Scientific Publications, 1986.

Fields, et al., eds., Fields Virology, $3^{rd}$ ed., vols. I and II, Lippencott et al, publishers, 1996.

Colligan, et al, eds., Current Protocols in Immunology, Wiley and Sons, NY, 2000.

Stewart et al., "Lentiviral delivery of HIV-1 Vpr protein induces apoptosis in transformed cells," Proceedings of the National Academy of Sciences of USA (1999) 96(21):12039-12043.

Ortman, B. et al., A Critical Role for Tapasin in the Assembly and Function of Multimeric MHC Class I-TAP Complexes.

Ortman, B. et al., A Critical Role for Tapasin in the Assembly and Function of Multimeric MHC Class I-TAP Complexes, (1997).

Utz and Anderson, "Life and death decisions: regulation of apoptosis by proteolysis of signaling molecules," Cell Death Differ. (2000) 7:569-602.

Sambrook, et al., Molecular Cloning: A Laboratory Manual ($2^{nd}$ Ed.), Cold Spring Harbor Laboratory Press, Clod Spring Harbor, NY, 1989.

Ausubel, et al., eds., Current Protocols in Molecular Biology, Wiley and Sons, NY, 2000.

Glover, ed., DNA Cloning: A Practical Approach, vols. 1 and II, (1985 and 1995).

Colwick and Kaplan, eds., Methods in Enzymology, Academic Press, 1966, 1975, 1982.

Weir and Blackwell, eds., Handbook of Experimental Immunology, vols. I-IV, Blackwell Scientific Publications, 1986.

Fields, et al., eds., Fields Virology, $3^{rd}$ ed., vols. I and II, Lippencott et al, publishers, 1996.

Colligan, et al, eds., Current Protocols in Immunology, Wiley and Sons, NY, 2000.

* cited by examiner

CHIMERIC PROTEINS FOR CELL TARGETING AND APOPTOSIS INDUCTION AND METHODS OF USING THE SAME

CROSS REFERENCE TO RELATED APPLICATION

This application is a U.S. National Phase Application of PCT International Application PCT/US02/16680, filed May 28, 2002, which claims priority to provisional application Ser. No. 60/293,794, filed May 25, 2001.

FIELD OF THE INVENTION

The invention relates to compositions and methods for selectively targeting cells for apoptosis induced cell death. The invention relates to compositions and methods for selectively targeting cells for cell death.

BACKGROUND OF THE INVENTION

The core protein of West Nile Virus (WNV) has recently been identified as being capable of inducing apoptosis in cell in which it is present. This observation is described in PCT Application Number PCT/US01/31355, which is incorporated herein by reference.

Similarly, the HIV accessory protein Vpr has been identified as being capable of cell cycle arrest and the induction of apoptosis. This observation is described in PCT application PCT/US01/10028, which is incorporated herein by reference.

In addition to these proteins, other proteins such as caspase have been known to induce apoptosis in cells.

There remains a need for compositions and methods which can incorporate the activity of apoptosis inducing proteins into effective compositions useful in methods of eliminating specific cells.

SUMMARY OF THE INVETION

The present invention provides fusion proteins which comprise an apoptosis inducing protein portion and a cell targeting portion.

The present invention provides compositions for and methods of targeting and inducing the death of cells. The present invention relates to a method of inducing cell death which comprises the step of contacting cells with an amount of a fusion protein which comprises an apoptosis inducing protein portion and a cell targeting portion. The fusion protein is administered in an amount effective to induce cell death.

The present invention provides fusion proteins which comprise a protease portion and a cell targeting portion. In one embodiment, the cell targeting portion comprises a ligand that binds to costimulatory molecule, cytokine receptors, chemokine receptors, growth factor receptors, oncogene products or a cancer cell marker.

The present invention provides compositions for and methods of targeting and inducing the death of cells. The present invention relates to a method of inducing cell death which comprises the step of contacting cells with an amount of a fusion protein which comprises an protease portion and a cell targeting portion. The fusion protein is administered in an amount effective to induce cell death

DETAILED DESCRIPTION OF THE PREFERRED EMBODIMENTS

As used herein, the term "apoptosis-inducing protein" and "AIP" are used interchangeably and meant to refer to proteins or fragments thereof which induce apoptosis in cell when they are present in such cells.

As used herein, the term "protease portion is meant to refer to the portions of fusion proteins which are protease sequences or fragments thereof which retain there ability to function as proteases or be converted into active proteases.

As used herein, the terms "induce" and "inducing" in reference to cell death or apoptosis refer to activities that initiate events that lead to cell death, including activities that initiate cellular events that are part of an apoptotic pathway that contribute to cell death.

As used herein, the term "apoptosis" refers to the form of eukaryotic cellular death, which is distinct form necrosis, and which includes cytoskeletal disruption, cytoplasmic shrinkage and condensation, expression of phosphatidylserine on the outer surface of the cell membrane and blebbing, resulting in the formation of cell membrane bound vesicles or apoptotic bodies. For a review of apoptotic cell death see, e.g., Utz & Anderson, 2000, Life and death decisions: regulation of apoptosis by proteolysis of signaling molecules, Cell Death Differ., 7:589-602.

As used in this specification and the appended claims, the singular forms "a," "an" and "the" include plural references unless the content clearly dictates otherwise. Thus, for example, reference to "a cell" includes a mixture of two or more cells.

As used herein, the phrases "amount effective to induce cell death" and "level effective to induce cell death" in reference to capsid protein, or functional fragments thereof, means that the amount of capsid protein, or functional fragment thereof, in contact with a cell, or the level of capsid protein, or functional fragment thereof, expressed in the cell, is effective to trigger the events that will kill the cell.

As used herein, the term "protein" refers to a polymer of amino acid residues, and is not limited to a minimum length. Polypeptides, peptides, oligopeptides, dimers, multimers, and the like, are included in the definition. Both full length proteins and fragments thereof are contemplated by the definition. The term also includes post-expression modifications to the protein, including, but not limited to, glycosylation, acetylation, phosphorylation.

As used herein, "injectable pharmaceutical composition" refers to pharmaceutically acceptable compositions for use in patients that are sterile, pyrogen-free, and free of any particulates. See, *Remington 's Pharmaceutical Sciences,* 18$^{th}$ Ed., Gennaro, ed., Mack Publishing Co., Easton, Pa., 1990 and U.S.P.

As used herein, "pharmaceutically acceptable carrier" includes any carrier that does not itself induce a harmful effect to the individual receiving the composition. For example, a "pharmaceutically acceptable carrier" should not induce the production of antibodies harmful to the recipient. Suitable "pharmaceutically acceptable carriers" are known to those of skill in the art and are described in *Remington 's Pharmaceutical Sciences,* supra.

As used herein, "hyperproliferating cells" refers to cells that are growing, dividing, or proliferating at an inappropriate or non-normal time or place, and includes cells that have entered the cell cycle when they should be in $G_0$ or in a quiescent state. For example, tumor cells are included within the meaning of "hyperproliferating cells." Diseases or conditions characterized by or associated with "hyperproliferating cells" include cancer, autoimmunity, non-malignant growths, and psoriasis.

As used herein, "treating" includes the amelioration and/or elimination of a disease or condition characterized by or associated with hyperproliferating cells.

As used herein, "individual" refers to human and non-human animals that can be treated with pharmaceutical compositions of the invention.

As used herein, the term "administering" includes, but is not limited to, intra-tumoral injection, transdermal, parenteral, subcutaneous, intramuscular, oral, and topical delivery.

As used herein, "intra-tumoral injection" in reference to administration of pharmaceutical compositions refers to the direct introduction of the pharmaceutical composition into a tumor site by injection.

The present invention arises out of the discovery of the apoptosis-inducing activity of the WNV capsid (Cp) protein in tumor-derived cells, the similar activity of HIV accessory protein Vpr, the apoptosis inducing activity of the mitochondrial protein AIF, and various other endogenous proteins such as Caspases. It has been discovered that the presence of these AIPs in cells leads to the induction of an apoptotic pathway and, ultimately, to the death of cells. The apoptosis-inducing activity of AIPs renders them useful in methods of killing rapidly growing cells, including cancer cells and immune cells involved in autoimmune disease.

According to some aspects of the present invention, fusion proteins are provided which comprise an AIP portion linked to a targeting portion which is a specific ligand for a protein expressed by the cell type which is to be targeted for destruction. The ligand may be a natural ligand, an antibody or fragment thereof or another type of molecule that binds with specificity to a cellular protein.

According to some aspects of the present invention, fusion proteins are provided with a protease portion linked to a targeting portion which is a specific ligand for a protein expressed by the cell type which is to be targeted for destruction. The ligand may be a natural ligand, an antibody or fragment thereof or another type of molecule that binds with specificity to a cellular protein. Examples of proteases are TAP.

Depending upon the cell being targeted for destruction, the fusion proteins are useful to treat a variety of diseases. For example, if the ligand targets an protein expressed by tumor cells, the fusion protein is useful to treat cancer and reduce or eliminate tumor burden. If the ligand targets an protein expressed by particularly immune cells, the fusion protein is useful to treat autoimmune disease. Other disease may be similarly treated by the selective elimination of cells.

In some embodiments, the ligand can be a known ligand for a target cellular protein.

Examples of ligands include ligands that are specific for costimulatory molecules, cytokines (ligand for cytokine receptor), growth factors (ligand for growth factor receptor) and chemokines (ligand for chemokine receptor). Other ligands are antibodies including recombinant antibodies, antibody fragments which specifically bind to target cellular proteins such as erbB2, PSMA, Flt-3, cytokine receptors, growth factor receptors and chemokine receptors. Examples of ligands include CD28 and CTLA-4 which are both natural ligands for CD80. CD28 is also a natural ligand for CD86. The natural ligand for CD40 is CD40L, the natural ligand for ICOSL is ICOS, the natural ligand for ICAM-1 is LFA-3, the natural ligand for 41BB is 41BBL, the natural ligand for MCSFR is MCSF, the natural ligand for FT3 is FL3L, the natural ligand for CCR2, CCR3 and CCR5 are MCP-3, and RANTES. Human proinflammatory cytokines include IL-1α binds to IL-1 receptors and TNF-α and TNF-β bind to TNF receptors. The Th1 cytokines include IL-2, IL-15, and IL-18, and Th2 cytokines include IL-4, IL-5 and IL-10 bind to their respective receptors. GM-CSF is another factor which may be used to target cells according to the invention.

The fusion protein may include a protease cleavage site between the AIP portion and the ligand portion or between the protease portion and the ligand portion. An example of such a cleavage site is the cleavage site recognized by a protease known to be present in the cell targeted for elimination.

The practice of the present invention employs conventional methods molecular biology and recombinant DNA techniques within the skill of the art. Such techniques are explained fully in the literature. See, e.g., Sambrook et al., eds., Molecular Cloning: A Laboratory Manual ($2^{nd}$ ed.) Cold Spring Harbor Laboratory Press, Cold Spring Harbor, N.Y. (1989); Ausubel et al., eds., Current Protocols in Molecular Biology, John Wiley & Sons, New York, N.Y. (2000); Glover, ed., DNA Cloning: A Practical Approach, Vols. I & II; Colowick & Kaplan, eds., Methods in Enzymology, Academic Press; Weir & Blackwell, eds., Handbook of Experimental Immunology, Vols. I-IV, Blackwell Scientific Pubs. (1986); Fields, Knipe, & Howley, eds., Fields Virology ($3^{rd}$ ed.) Vols. I & II, Lippincott Williams & Wilkins Pubs. (1996); Coligan et al., eds., Current Protocols in Immunology, John Wiley & Sons, New York, N.Y. (2000), each of which is incorporated herein by reference.

The identification of functional fragments of proteins that induce apoptosis can be undertaken and achieved routinely capsid protein. Likewise, the identification of ligands can be routinely achieved. The construction of fusion proteins which comprise an AIP portion that retains its activity and ligand portion that retains its activity can be accomplished. One having ordinary skill in the art can readily determine whether fusion protein will target the cell and induce apoposis.

Therapeutic aspects of the invention include use of the fusion proteins to treat diseases associated with hyperproliferating cells such as cancer or psoriasis and autoimmune disease by selectively targeting cells for apoptosis induced death. The present invention relates to pharmaceutical compositions that comprise such fusion proteins. Pharmaceutical compositions of the present invention are particularly useful for treating cancer characterized by solid tumors. The ability to stimulate hyperproliferating cells to undergo apoptotic death provides a means to disrupt the hyperproliferation of the cells, thereby decreasing the tumor. In diseases such as cancer and psoriasis which are characterized by the inappropriate hyperproliferation of cells, the pharmaceutical composition is useful to arrest the hyperproliferation through an induction of an apoptotic cell death, thereby effectuating a treatment of the disease.

WNV capsid protein, or functional fragments thereof, may be produced by routine means using readily available starting materials as described above. The nucleic acid sequence encoding WNV capsid protein as well as the amino acid sequence of the protein are well known. The entire genome for a number of WNV isolates are published and available in GenBank, including isolate 2741 (accession number AF206518), strain NY99-flamingo382-99 (accession number AF196835), and the isolate identified as accession number M12294, each of which is incorporated herein by reference. There are a variety of publications relating to sequence information for the WNV genome, citations of which are linked to the sequence information in GenBank. Each of these references, including the publicly available sequence information, are incorporated herein by reference.

Sequence information for capsid proteins and nucleic acids from other Flaviviridae viruses can also be found in GenBank. By way of non-limiting examples, complete genome sequences of strains and isolates provided in GenBank include, JEV (accession number M18370, D90194, and D90195), SLEV (accession number M16614), YFV (accession numbers AF094612, U17067, U17066, U54798, U21055, U21056, and X03700), DENV (accession numbers M23027, U88535, U88536, and U88537), BVDV (accession number M31182), and HIV (accession number AF207773 and AF207774), each of which is incorporated herein by reference. Other AIP sequences such as HIV Vpr and various caspases are well known. The amino acid sequence of Vpr is disclosed in U.S. Ser. No. 08/167,608 filed Dec. 15, 1993, which is incorporated herein by reference. Data from Vpr protein mapping experiments to identify regions that specifically interact with and arrest cell cycle arrest are described in Provisional Application 60/055,754 filed Aug. 14, 1997, which is incorporated herein by reference.

One having ordinary skill in the art may use commercially available expression vectors and systems or produce vectors using well known methods and readily available starting materials to produce the fusion proteins. Expression systems containing the requisite control sequences, such as promoters and polyadenylation signals, and preferably enhancers, are readily available and known in the art for a variety of hosts. See, e.g., Current Protocols in Molecular Biology, John Wiley & Sons, New York, N.Y. (2000). Thus, the desired proteins can be prepared in both prokaryotic and eukaryotic systems, resulting in a spectrum of processed forms of the protein.

The most commonly used prokaryotic system remains *E. coli*, although other systems such as *Bacillus subtilis* and *Pseudomonas* are also useful. Suitable control sequences for prokaryotic systems include both constitutive and inducible promoters including, but not limited to, the lac promoter, the tip promoter, hybrid promoters such as the tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast cells, fungal cells, insect cells, mammalian cells, avian cells, and cells of higher plants. Suitable promoters are available which are compatible and operable for use in each of these host cell types. Also available, are termination sequences and enhancers, such as, for example, the baculovirus polyhedron promoter. As described above, promoters can be either constitutive or inducible. For example, in mammalian systems, the mouse metallothionine promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the fusion protein produced using such expression systems.

In addition to producing these proteins by recombinant techniques, automated amino acid synthesizers may also be employed to produce fusion proteins. It should be further noted that if the proteins herein are made synthetically, substitution by amino acids which are not encoded by the gene may also be made. Alternative residues include, for example, the amino acids of the formula $H_2N(CH_2)_nCOOH$ wherein n is 2-6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

Pharmaceutical compositions used for treating autoimmune diseases and diseases characterized by hyperproliferating cells comprising fusion protein and a pharmaceutically acceptable carrier or diluent may be formulated by one of skill in the art with compositions selected depending upon the chosen mode of administration. Suitable pharmaceutical carriers are described in *Remington's Pharmaceutical Sciences*, supra., a standard reference text in this field.

A common requirement for any route of administration is efficient and easy delivery. In one embodiment of the invention, the compositions are administered by injection. In a preferred embodiment, the compositions are administered by intra-tumoral injection. Other means of administration include, but are not limited to, transdermal, transcutaneous, subcutaneous, intraperitoneal, mucosal, or general persistent administration.

For parenteral administration, the Flaviviridae capsid protein, or functional fragment thereof, can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

Although individual needs may vary, the determination of optimal ranges for effective amounts of formulations is within the skill of the art. Human doses can also readily be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3 In: Goodman & Gilman's The Pharmacological Basis of Therapeutics, 9th Ed., Hardman et al., eds., McGraw-Hill, New York, N.Y., 1996). Usually, a daily dosage of fusion protein can be about 1 µg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions comprising fusion protein may be administered by any means that enables the active agent to reach the agent's site of action in the body of the recipient. Because proteins are subject to digestion when administered orally, parenteral administration, i.e., intravenous, subcutaneous, intramuscular, would ordinarily be used to optimize absorption. In addition, the pharmaceutical compositions of the present invention may be injected at a site at or near hyperproliferative growth. For example, administration may be by direct injection into a solid tumor mass or in the tissue directly adjacent thereto. If the individual to be treated is suffering from psoriasis, the fusion protein may be formulated with a pharmaceutically acceptable topical carrier and the formulation may be administered topically as a creme, lotion or ointment for example.

EXAMPLE

The following sequences identified by accession number and references are incorporated herein by reference.

| West Nile Virus | AF202541 | strain HNY1999 |
| West Nile Virus | NC 001563 | complete genome |
| HIV Vpr | | |
| VPR | AJ404325 | vpr, gag, pol, vif, vpu, env, and nef |
| VPR | AF316862 | vif, vpr (Cameroon isolate) |
| VPR | AF325763 | vif, vpr (South African isolate) |
| AIF | | |
| AIF | XM 010246 | also called "programmed cell death 8" or "PDCD8" |
| AIF | NM 004208 | |
| TAP | | |
| TAP | AF009510 | also called tapasin |
| TAP | AF314222 | alternatively spliced |
| TAP | AB010639 | Tapasin 2 |

Macrophage Colony-Stimulating Factor
Accession No. AAA59572
Cerretti, D. P. et al., Mol. Immunol. 25 (8), 761-770 (1988)
Accession No. AAB51235
Visvader, J. and Verma, I. M., Mol. Cell. Biol. 9 (3) 1336-1341 (1989)
Accession No. P09603: Wong et al. Science 235 (4795) 1504-1508 (1987)
Cerretti et al. Mol. Immunol. 25 (8) 761-770 (1988)
Kawasaki et al., Science 230 (4723) 291-296 (1985)

Chemokine (C-C motif) Receptor 5
Accession No. 4502639
Raport, C. J. et al., J. Biol. Chem. 271 (29), 17161-17166 (1996)

Monocyte Chemoattractant Protein (MCP-3)
Accession No. CAA50407
Minty, A. et al., Eur. Cytokine Netw. 4 (2), 99-110 (1993)
Accession No. AAC03538 pFLT3 fms-related tyrosine kinase 3
Accession No. 4758396
Small, D. et al., Proc. Natl. Acad. Sci. U.S.A. 91, 459-463 (1994)
Accession No. P36888
Small et al., Proc. Natl. Acad. Sci. U.S.A. 91, 459-463 (1994)

pFLT3LG fms-related tyrosine kinase 3 ligand
Accession No. 4503751

4-1BB
Accession No. AAA53133
Alderson, M. R. et al., Eur. J. Immunol. 24 (9), 2219-2227 (1994)

4-1BBL
Accession No. P41273
Alderson, M. R. et al., Eur. J. Immunol. 24 (9) 2219-2227 (1994)

RANTES
Accession No. BAA76939
Liu, H. et al., PNAS U.S.A. 96 (8), 45814585 (1999)
Accession No. 1065018
Accession No. XM 012656
Accession No. NM 002985

CCR1/MIP1R
Accession No. P32246
Neote, K. et al., Cell 72 (3) 415-425 (1993)
Gao, J. L. et al., J. Exp. Med. 177 (5) 1421-1427 (1993)
Nomura, H. et al., Int. Immunol. 5 (10) 1239-1249 (1993)

CCR5
Accession No. P56493
Kuhmann, S. E. et al., J. Virol. 71 (11) 8642-8656 (1997)
Murayama, Y. et al.

CCR2
Accession No. P41597
Charo, I. F. et al., PNAS, U.S.A. 91 (7) 2752-2756 (1994)
Yamagami, S. et al., Biochem. Biophys. Res. Commun. 202 (2) 1156-1162 (1994)
Wong, L. M. et al., J. Biol. Chem. 272 (2) 1038-1045 (1997)

CCR3
Accession No. P51677
Combadiere, C. et al., J. Biol. Chem. 270 (28) 16491-16494 (1995)
Combadiere, C. et al., J. Biol. Chem. 270 30235 (1995)
Dougherty, B. L. et al., J. Exp. Med. 183 (5) 2349-2354 (1996)

CD40 ligand
Accession No. P29965
Graf, D. et al., Eur. J. Immunol. 22 (12) 3191-3194 (1992)
Hollenbaugh, D. et al., Embo. J. 11 (12) 4313-4321 (1992)
Spriggs, M. K. et al., Cell 72 291-300 (1993)
Spriggs, M. K. et al., J. Exp. Med. 176 (6) 1543-1550 (1992)
Gauchat et al., Febs. Lett. 315 (3) 259-266 (1993)

CD86
Accession No. 5901920
Azuma et al., Nature 366 (6450) 76-79 (1993)
Reeves et al., Mamm. Genome 8 (8) 581-582 (1997)

CD80
Accession No. 4885123
Selvakumar et al., Immunogenetic 36 (3) 175-181 (1992)
Freeman et al., Blood 79 (2) 489-494 (1992)

CD40
Accession No. 4507581
Stamenkovic et al., Embo. J. 8 (5) 1403-1410 (1989)

LFA-3
Accession No. BAA05922

ICAM1
Accession No. AAB51145

CD28
Accession No. 5453611
Lee et al., J. Immunol. 145 (1) 344-352 (1990)

The nucleotide and amino acid sequences of human IL-1α are well known and set forth in Telford, et al. (1986) Nucl. Acids Res. 14:9955-9963, Furutani, et al. (1985) Nucl. Acids Res. 14:3167-3179, March, et al. (1985) Nature 315:641-647, and accession code Swissprot PO1583, which are each incorporated herein by reference.

The nucleotide and amino acid sequences of human IL-2 are well known and set forth in Holbrook, et al. (1984) Proc. Natl. Acad. Sci. USA 81:1634-1638, Fujita, et al. (1983) Proc. Natl. Acad. Sci. USA 80:7437-7441, Fuse, et al. (1984) Nucl. Acids Res. 12:9323-9331, Taniguchi, et al. (1983) Nature 302:305-310, Maeda, et al. (1983) Biochem. Biophys. Res. Comm. 115:1040-1047, Devos, et al. (1983) Nucl. Acids Res. 11:4307-4323, and accession code Swissprot PO1585, which are each incorporated herein by reference.

The nucleotide and amino acid sequences of human IL-4 are well known and set forth in Arai, et al. (1989) J. Immunol. 142:274-282, Otsuka, et al. (1987) Nucl. Acids Res. 15:333-344, Yokota, et al. (1986) Proc. Natl. Acad. Sci. USA 83:5894-5898, Noma, et al. (1984) Nature 319:640-646, Lee, et al. (1986) Proc. Natl. Acad. Sci. USA 83:2061-2063, and accession code Swissprot 05112 (the accession code for murine IL-4 is Swissprot 07750), which are each incorporated herein by reference.

The nucleotide and amino acid sequences of human IL-5 are well known and set forth in Campbell, et al. (1987) Proc. Natl. Acad. Sci. USA 84:6629-6633, Tanabe, et al. (1987) J. Biol. Chem. 262:16580-16584, Campbell, et al. (1988) Eur. J. Biochem. 174:345-352, Azuma, et al. (1986) Nucl. Acids Res. 14:9149-9158, Yokota, et al. (1986) Proc. Natl. Acad. Sci. USA 84:7388-7392, and accession code Swissprot PO5113, which are each incorporated herein by reference.

The nucleotide and amino acid sequences of human IL-10 are well known and set forth in Viera, et al. (1991) Proc. Natl. Acad. Sci. USA 88:1172-1176, and accession code Swissprot P22301.

The nucleotide and amino acid sequences of human IL-15 are well known and set forth in Grabstein, et al. (1994) Science 264:965-968, and accession code Swissprot U03099, which are each incorporated herein by reference.

The nucleotide and amino acid sequences of human IL-18 are well known and set forth in Ushio, et al. (1996) J. Immunol. 156:4274-4279, and accession code D49950, which are each incorporated herein by reference.

The nucleotide and amino acid sequences of human TNF-α are well known and set forth in Pennica, (1984) Nature 312: 724-729, and accession code Swissprot PO1375, which are each incorporated herein by reference.

The nucleotide and amino acid sequences of human TNF-β are well known and set forth in Gray, (1984) Nature 312:721-724, and accession code Swissprot PO1374, which are each incorporated herein by reference.

The invention claimed is:

1. A fusion protein comprising an apoptosis-inducing protein (AIP) portion and a ligand portion, wherein the AIP portion is from a *Flaviviridae* capsid and wherein the ligand portion binds to a costimulatory molecule, cytokine receptor, chemokine receptor, growth factor receptor, oncogene product, or cancer cell marker.

2. A fusion protein comprising an apoptosis-inducing protein (AIP) portion and a ligand portion, wherein the AIP portion is from WNV capsid and wherein the ligand portion binds to a costimulatory molecule, cytokine receptor, chemokine receptor, growth factor receptor, oncogene product, or cancer cell marker.

3. The fusion protein of claim 1 wherein the ligand is an antibody or an antibody fragment.

4. The fusion protein of claim 3 wherein the ligand is an antibody or antibody fragment tat binds to erbB2 protein, PSMA protein or Flt-3.

5. A method of eliminating a cell that expresses an oncogene product, or a cancer cell marker comprising contacting the cell with a fusion protein of claim 1 by direct application of the fusion protein to the cell.

6. A method of eliminating cells that express an oncogene product, or cancer cell marker in an individual comprising administering to said individual a fusion protein of claim 1 by direct application of the fusion protein to the cell.

7. The fusion protein of claim 1 wherein the ligand binds to a cancer cell marker.

8. The fusion protein of claim 1 wherein the ligand binds to erbB2 protein.

9. The fusion protein of claim 2 wherein the AIP portion is from WNV capsid and the ligand is an antibody or an antibody fragment.

10. The fusion protein of claim 2 wherein the AIP portion is from WNV capsid and the ligand binds to a cancer cell marker.

11. The fusion protein of claim 2 wherein the AIP portion is from WNV capsid and the ligand is an antibody or an antibody fragment that binds to a cancer cell marker.

12. The fusion protein of claim 2 wherein the AIP portion is from WNV capsid and the ligand binds to erbB2 protein.

13. The fusion protein of claim 2 wherein the AIP portion is from WNV capsid and the ligand is an antibody or an antibody fragment that binds to erbB2 protein.

14. A method of eliminating a cell comprising contacting the cell with a fusion protein of claim 13 by direct application of the fusion protein to the cell.

15. A method of eliminating cells in an individual comprising administering to said individual a fusion protein of claim 13 by direct application of the fusion protein to the cell.

16. The fusion protein of claim 1 wherein the AIP portion is from a *Flaviviridae* capsid from a virus selected from the group consisting of: Japanese Encephalitis virus, St. Louis encephalitis virus, Yellow fever virus, Dengue virus, Bovine viral diarrhea virus 1 and Hepatitis C virus.

17. The fusion protein of claim 1 wherein the ligand binds to erbB2 protein, PSMA protein, or Flt-3.

18. The method of claim 5, wherein the cell is a tumor cell.

19. A pharmaceutical composition comprising:
 (i) a fusion protein comprising an apoptosis-inducing protein (AIP) portion and a ligand portion, wherein the AIP portion is from a *Flaviviridae* capsid and wherein the ligand portion binds to a oncogene product, or cancer cell marker; and
 (ii) a pharmaceutically acceptable carrier or diluent.

20. A method of treating an individual with cancer by administration of the pharmaceutical composition of claim 19.

\* \* \* \* \*

UNITED STATES PATENT AND TRADEMARK OFFICE
CERTIFICATE OF CORRECTION

| | | |
|---|---|---|
| PATENT NO. | : 7,592,012 B2 | Page 1 of 1 |
| APPLICATION NO. | : 10/478741 | |
| DATED | : September 22, 2009 | |
| INVENTOR(S) | : Weiner | |

It is certified that error appears in the above-identified patent and that said Letters Patent is hereby corrected as shown below:

On the title page,

[*] Notice:    Subject to any disclaimer, the term of this patent is extended or adjusted under 35 USC 154(b) by 732 days Delete the phrase "by 732 days" and insert -- by 899 days --

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,592,012 B2  Page 1 of 1
APPLICATION NO. : 10/478741
DATED : September 22, 2009
INVENTOR(S) : David B. Weiner It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1568 days.

Signed and Sealed this

Twenty-first Day of September, 2010

David J. Kappos
*Director of the United States Patent and Trademark Office*